United States Patent
Hiei et al.

(10) Patent No.: US 8,114,033 B2
(45) Date of Patent: Feb. 14, 2012

(54) SLEEP DETERMINATION APPARATUS

(75) Inventors: Takehiko Hiei, Osaka (JP); Kazuhisa Shigemori, Shiga (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 12/446,944

(22) PCT Filed: Nov. 19, 2007

(86) PCT No.: PCT/JP2007/072396
§ 371 (c)(1),
(2), (4) Date: Apr. 23, 2009

(87) PCT Pub. No.: WO2008/069017
PCT Pub. Date: Jun. 12, 2008

(65) Prior Publication Data
US 2010/0030118 A1    Feb. 4, 2010

(30) Foreign Application Priority Data
Dec. 8, 2006   (JP) ................................ 2006-331654

(51) Int. Cl.
*A61B 5/103* (2006.01)
*A61B 5/117* (2006.01)

(52) U.S. Cl. ........................................ 600/595; 600/587

(58) Field of Classification Search .................. 600/300, 600/301, 587, 595; 702/127, 150, 152, 153
See application file for complete search history.

(56) References Cited

U.S. PATENT DOCUMENTS
5,479,939 A  *  1/1996  Ogino ........................... 600/595

FOREIGN PATENT DOCUMENTS
| | | |
|---|---|---|
| JP | 4-272746 A | 9/1992 |
| JP | 5-159173 A | 6/1993 |
| JP | 2817358 B2 | 10/1998 |
| JP | 2005-124858 A | 5/2005 |
| JP | 2006-181263 A | 7/2006 |
| JP | 2007-252747 A | 10/2007 |

* cited by examiner

*Primary Examiner* — Jeffrey G Hoekstra
(74) *Attorney, Agent, or Firm* — Birch, Stewart, Kolasch & Birch, LLP.

(57) ABSTRACT

A sleep determination apparatus capable of detecting wakefulness of a subject before entering a hypnagogic state with high accuracy is provided.

When the subject is not yet in the hypnagogic state, it is determined that the subject is asleep when a detected body movement signal continuously remains below a determination threshold for a predetermined time or longer, and that the subject is awake in other situations. When the subject has entered the hypnagogic state, it is determined that the subject is awake when the detected body movement signal continuously remains above the determination threshold for the predetermined time or longer, and that the subject is asleep in other situations.

3 Claims, 8 Drawing Sheets

FIG. 5
(a)
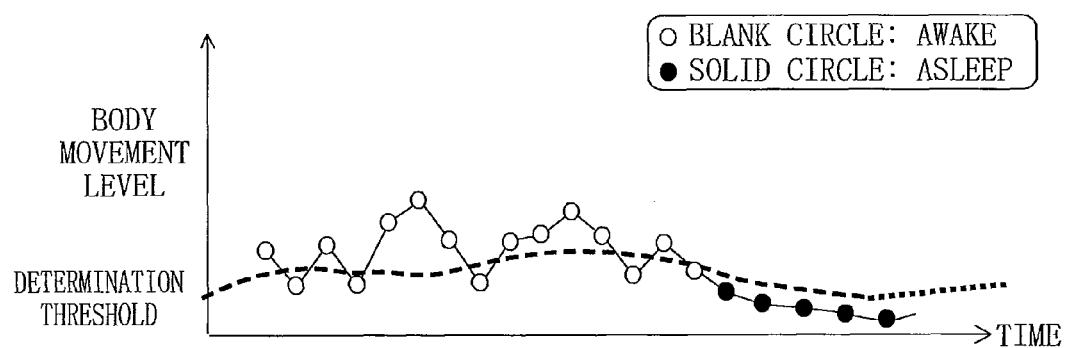
(b)
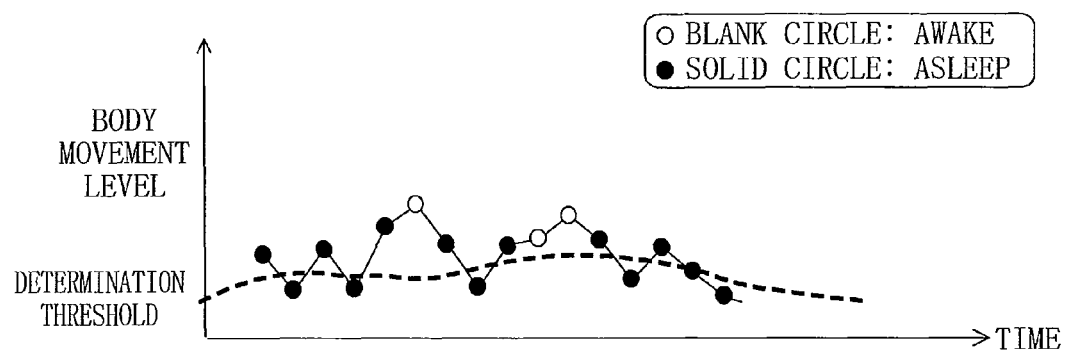

FIG. 8

| | MEASURE-MENT DATE | A: TIME WHEN SUBJECT ENTERS BED | B: TIME WHEN SUBJECT ENTERS HYPNAGOGIC STATE | PERIOD FROM ENTRANCE TO BED TO ENTRANCE TO HYPNAGOGIC STATE (B-A) [min] | DETERMINED PERIOD OF WAKEFULNESS (INCLUDING PERIOD WHEN SUBJECT IS NOT PRESENT) [min] | RATE OF CORRECT WAKEFULNESS DETERMINATION [%] |
|---|---|---|---|---|---|---|
| CONVENTIONAL METHOD | 7/9 | 23:35 | 0:53 | 78 | 17 | 22 |
| | 7/10 | 22:18 | 0:20 | 122 | 34 | 28 |
| | 7/11 | 23:03 | 0:20 | 77 | 27 | 35 |
| | 7/13 | 23:14 | 1:00 | 106 | 36 | 34 |
| | TOTAL | | | 383 | 114 | 30 |
| METHOD OF PRESENT INVENTION | 8/5 | 22:15 | 0:19 | 124 | 81 | 65 |
| | 8/6 | 22:43 | 23:54 | 71 | 56 | 79 |
| | 8/8 | 23:01 | 0:01 | 60 | 29 | 48 |
| | TOTAL | | | 255 | 166 | 65 |

SLEEP DETERMINATION APPARATUS

TECHNICAL FIELD

The present invention relates to sleep determination apparatuses, particularly to improvement in the accuracy of determining wakefulness of a subject before entering a hypnagogic state.

BACKGROUND ART

There are conventionally known sleep determination apparatuses for determining whether a subject is asleep or not based on an output signal (a body movement signal) obtained by detecting body movement of the subject. For example, Patent Document 1 discloses a sleep determination apparatus which determines that a subject is in a hypnagogic state when an output signal obtained by detecting the subject's body movement continuously remains between a first threshold and a second threshold for a predetermined time.
Patent Document 1: Published Japanese Patent No. 2817358

DISCLOSURE OF THE INVENTION

Problem that the Invention is to Solve

For health care of the subject, control of air conditioners and lightening equipment, and the like, it is important to determine whether the subject is asleep or awake before and after the subject enters the hypnagogic state, in addition to the above-described determination whether or not the subject is in the hypnagogic state.

For example, as a determination method for the sleep determination apparatus of Patent Document 1, it may be determined that the subject is awake when the body movement signal continuously remains above a certain threshold for a predetermined time, and that the subject is asleep in other situations.

According to this method, however, when the subject is reading a book or using a personal computer on a bed before entering the hypnagogic state, the subject may continuously produce movement which is not very large. In this case, it is difficult to distinguish this body movement from body movement associated with heartbeat and respiration (small body movement). Therefore, the subject, who is actually awake, may erroneously be determined as being asleep, depending on the selected threshold. That is, according to the above-described determination method, the accuracy in determining whether the subject before entering the hypnagogic state is awake or not is significantly reduced.

The present invention was developed in view of the foregoing, and the present invention aims to obtain a sleep determination apparatus capable of accurately detecting wakefulness of the subject before entering a hypnagogic state.

Means of Solving the Problem

For the above-described purpose, a sleep determination apparatus (10) of the present invention determines, when a subject is not yet in the hypnagogic state, that the subject is asleep when the body movement signal from the subject continuously remains below a determination threshold for a predetermined period, and that the subject is awake in other situations. That is, a stringent criterion is imposed on the determination whether the subject is asleep or not, so that the subject who is actually awake is not erroneously determined as being asleep.

Specifically, a first aspect of the invention relates to a sleep determination apparatus including: a body movement detection means (20) attached to a bedding (1) to detect body movement of a subject and output the body movement as a body movement signal; a hypnagogic state determination means (43) which determines whether the subject is in a hypnagogic state or not based on the body movement signal; and a first sleep determination means (46) which determines, when the hypnagogic state determination means (43) determines that the subject is not in the hypnagogic state, that the subject is asleep when the body movement signal continuously remains below a determination threshold for a predetermined time or longer, and that the subject is awake in other situations.

In this structure, when the body movement signal which is associated with the subject's body movement and output from the body movement detection means (20) continuously remains below the determination threshold for the predetermined time or longer, it is determined that the subject is asleep (hereinafter, this method may be referred to as an example determination method of the invention). Therefore, a determination whether the subject is asleep or not is made on a more stringent criterion as compared with, for example, the case where the subject is determined as being awake when the body movement signal continuously remains above the determination threshold for the predetermined time or longer (hereinafter, this method is referred to as a conventional determination method). As a result, the rate at which the subject is determined as being awake is increased.

Specifically, in the conventional determination method, when the body movement signal does not continuously remain above the determination threshold for the predetermined time or longer, i.e., in a period during which the subject is not determined as being awake, it is determined that the subject is asleep. Therefore, when the subject who is not yet in the hypnagogic state and awake produces small body movement, and the body movement signal does not remain above the determination threshold for the predetermined time or longer, the subject is determined as being asleep. In contrast to this, in the example determination method of the present invention, when the subject's body movement signal exceeds the determination threshold for only a short time in the predetermined time, it is determined that the subject is not asleep, i.e., the subject is awake. Thus, the state of the subject before entering the hypnagogic state can be determined with accuracy.

In the above-described structure, the sleep determination apparatus further includes a second sleep determination means (45) which determines, when the hypnagogic state determination means (43) determines that the subject is in the hypnagogic state, that the subject is awake when the body movement signal continuously remains above the determination threshold for the predetermined time or longer, and that the subject is asleep in other situations (a second aspect of the invention).

This structure makes it possible to prevent an erroneous determination that the subject is awake when noise, such as sound of a closing door, is generated after the subject has entered the hypnagogic state. The subject is basically in the asleep state after the subject has entered the hypnagogic state. Therefore, since the subject is determined as being awake only when the body movement signal continuously remains above the determination threshold for the predetermined time or longer, the erroneous determination, which may be made when noise is detected as the body movement signal, can be prevented.

As described above, by changing the determination method before and after the subject enters the hypnagogic state, a determination of the subject's sleep can be made by a determination method suitable for the state before and after the entrance to the hypnagogic state. Thus, the erroneous determination can be prevented as much as possible.

The predetermined time is preferably 3 minutes (a third aspect of the invention). Specifically, before entering the hypnagogic state, the subject is determined as being asleep when the body movement signal continuously remains below the determination threshold for 3 minutes or longer. After entering the hypnagogic state, the subject is determined as being awake when the body movement signal continuously remains above the determination threshold for 3 minutes or longer. In this way, as a period for change in sleep rhythm which is considered most appropriate from a viewpoint of hypnology is determined as the predetermined time, whether the subject is asleep or awake can be determined more accurately.

It is preferable that the sleep determination apparatus further includes a determination threshold setting means (42) which sets and updates the determination threshold based on a minimum value of the body movement signal in every given time (a fourth aspect of the invention). The body movement signal is expressed as a signal waveform formed by superimposing a small movement signal derived from respiration and heartbeat on a large movement signal derived from the subject's coming in/out of the bed, rolling over, and other body movements. As described above, for determining whether the subject is awake or asleep, the determination is made based on whether the large movement signal is continuously detected or not. Therefore, it is necessary to obtain a boundary level between the small movement signal and the large movement signal as a body movement determination threshold. When the subject is lying on the bed, the body movement detection means (20) can reliably detect the small movement signal derived from respiration and heartbeat. Therefore, the minimum value of the body movement signal is a value corresponding to the boundary level between the small movement signal and the large movement signal. Thus, by suitably updating the body movement determination threshold based on the minimum value of the body movement signal in every given time, an accurate body movement determination threshold corresponding to the boundary level between the small and large movement signals can be obtained.

The hypnagogic state determination means (43) is configured to determine that the subject is in the hypnagogic state when the first sleep determination means (46) determines that the subject is continuously asleep for a specified time or longer (a fifth aspect of the invention). Therefore, the hypnagogic state can be determined accurately based on the body movement signal.

Effect of the Invention

As described above, the sleep determination apparatus (10) of the present invention determines, when the subject is not yet in the hypnagogic state, that the subject is asleep when the body movement signal of the subject continuously remains below the determination threshold for a predetermined time or longer, and that the subject is awake in other situations. Therefore, a determination whether the subject before entering the hypnagogic state is asleep or not can be made stringently. Thus, an erroneous determination that the subject is asleep, though he is actually awake, can be prevented.

According to the second aspect of the invention, after the subject entered the hypnagogic state, whether the subject is asleep or awake is determined by the second sleep determination means which determines that the subject is awake when the body movement signal of the subject continuously remains above the determination threshold for the predetermined time or longer, and that the subject is asleep in other situations. Therefore, whether the subject is asleep or awake can be determined more accurately without being affected by noise, and the like.

According to the third aspect of the invention, the predetermined time is determined as 3 minutes. Therefore, whether the subject is asleep or awake can be determined with more reliability because a period for change in sleep rhythm which is considered most appropriate from a viewpoint of hypnology is determined as the predetermined time.

According to the fourth aspect of the invention, the determination threshold setting means (42) sets and updates the determination threshold based on a minimum value of the body movement signal in every given time. Therefore, the determination threshold can be updated based on the small movement signal reliably detected by the body movement detection means (20). In updating the determination threshold based on the body movement signal, whether the subject is asleep or not is determined stringently before the subject enters the hypnagogic state, and whether the subject is awake or not is determined stringently after the subject entered the hypnagogic state. Thus, an erroneous determination which may occur before and after the entrance to the hypnagogic state can be prevented.

According to the fifth aspect of the invention, the subject is determined as being in the hypnagogic state when it is determined that the subject is continuously asleep for a longer time than the predetermined time. Therefore, whether the subject is in the hypnagogic state or not can be determined more accurately, and the sleep determination of the subject can be made more accurately.

BRIEF DESCRIPTION OF DRAWINGS

FIG. 5(a) is a graph illustrating an example of sleep determination results before a subject enters a hypnagogic state, and FIG. 5(b) is a graph illustrating an example of sleep determination results after the subject entered the hypnagogic state.

FIG. 8 is a table of comparison between the conventional sleep determination method and the sleep determination method of the present invention in terms of rate of wakefulness determination.

EXPLANATION OF REFERENCE NUMERALS

Figure 1:
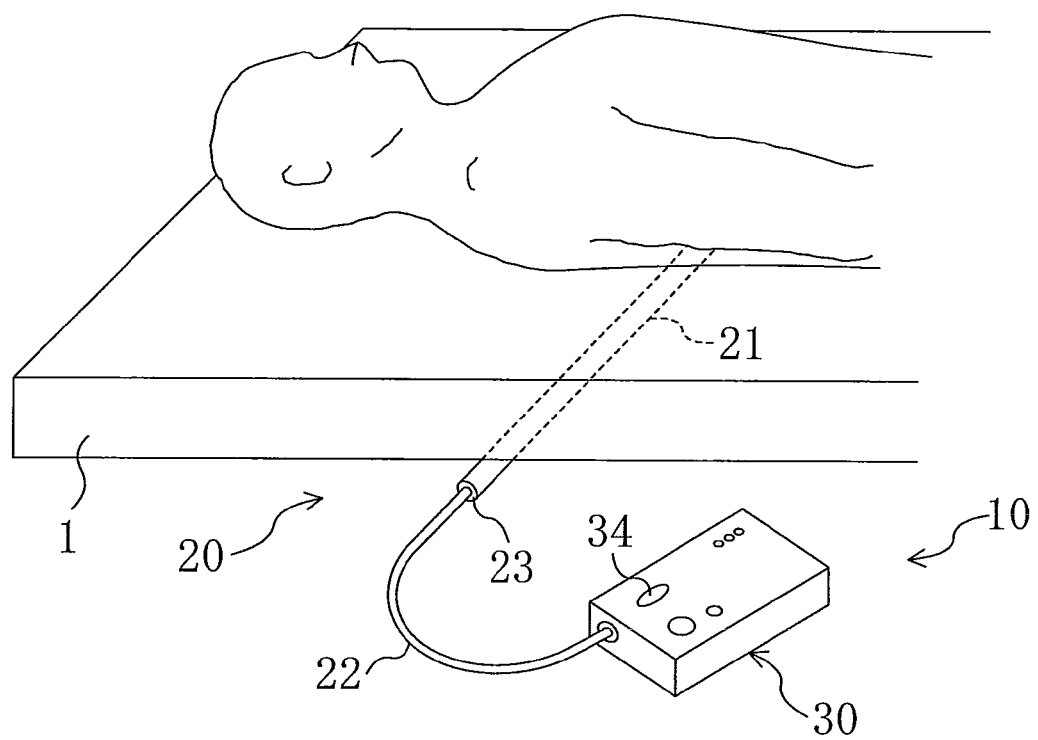
FIG. 1 is a schematic view illustrating how a sleep determination apparatus according to an embodiment of the present invention is used.

1 Bedding
10 Sleep determination apparatus
20 Sensor (body movement detection means)
42 Determination threshold setting means 43 Hypnagogic state determination means
45 In-hypnagogic-state determination means (first sleep determination means)
46 Pre-hypnagogic-state determination means (second sleep determination means)

BEST MODE FOR CARRYING OUT THE INVENTION

Hereinafter, an embodiment of the present invention will be described with reference to the accompanying drawings. It should be noted that the following description of the preferred embodiments is provided only for explanation purpose and does not limit the present invention, an object to which the present invention is applied, and use of the invention.

A body movement determination system (10) according to an embodiment of the present invention detects behavior of body movement of a subject, so that the detected data can be used for health care of the subject. Specifically, the body movement determination system (10) collects and stores data related to the body movement necessary for determining the subject's sleep, and outputs the data to a separate display device not shown. For this reason, the body movement determination system (10) includes a sensor (20) for detecting the body movement of the subject, and a main body (30) for processing and storing the detected signals.

Figure 2:
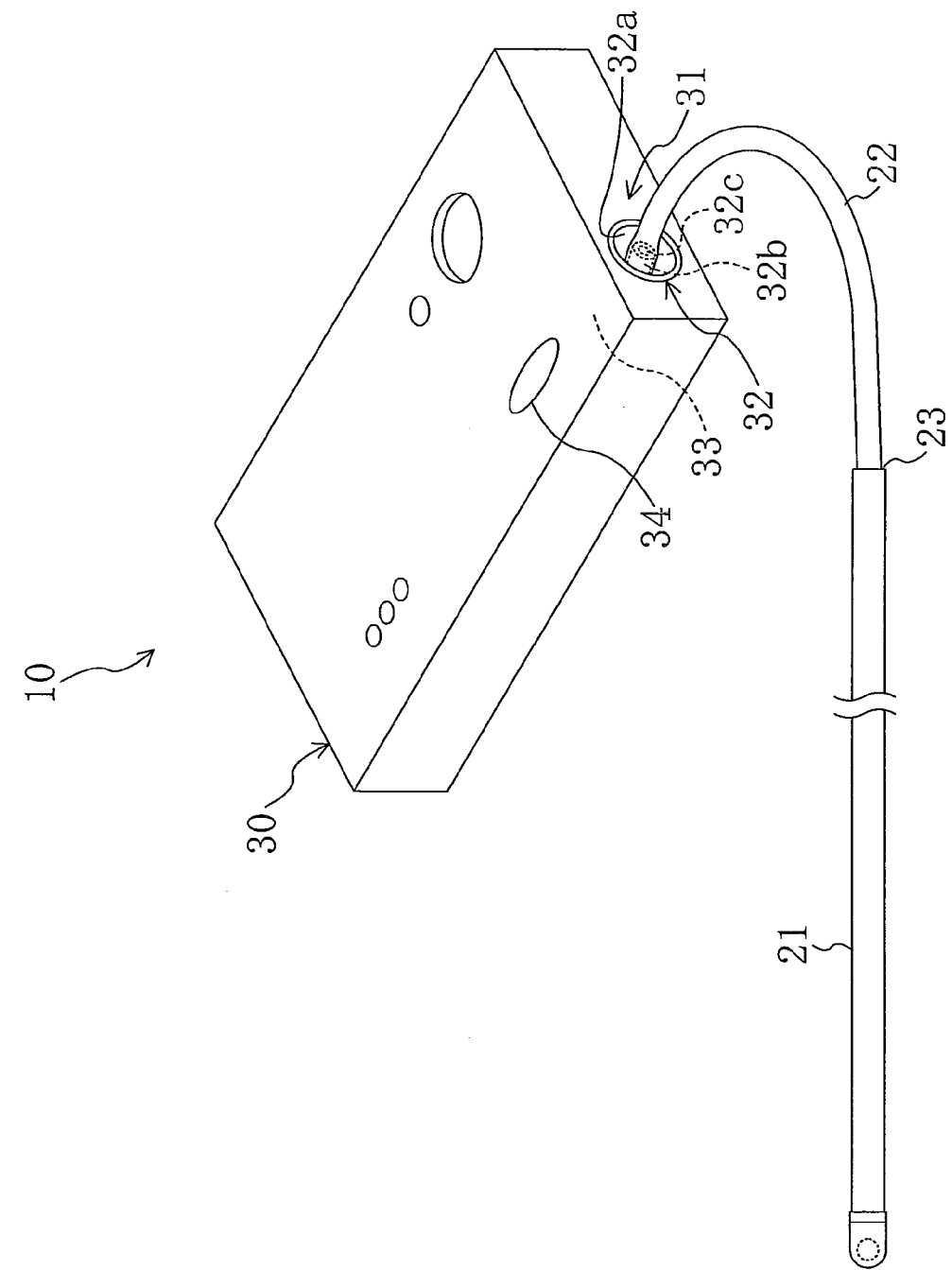
FIG. 2 is a perspective view illustrating the whole structure of the sleep determination apparatus.

As shown in FIGS. 1 and 2, the sensor (20) is a tube-like member configured to detect externally applied pressure to transmit it to the main body (30). Specifically, the sensor (20) includes a pressure sensing part (21) for detecting vibration associated with the subject's body movement as pressure variation, and a pressure transmitting part (22) for transmitting the pressure variation to the main body (30). The sensor (20) constitutes a body movement detection means which detects the subject's body movement as a body movement signal.

As shown in FIG. 1, the pressure sensing part (21) is constituted of a narrow and hollow tube, and arranged under a bedding (1), e.g., a mattress. The pressure transmitting part (22) is also constituted of a hollow tube, like the pressure sensing part (21), and connected to the pressure sensing part (21) through a connecting part (23). The pressure sensing part (21) is larger in diameter than the pressure transmitting part (22). When the subject lies on the bed, pressure and vibration are transmitted to the pressure sensing part (21) as the subject moves. Then, internal pressure of the pressure sensing part (21) is transmitted to the pressure transmitting part (22), and acts on a pressure receiving part (31) of the main body (30).

The pressure receiving part (31) is embedded in the box-shaped main body (30), and has an attachment part (32) capable of engaging with an end of the pressure transmitting part (22) opposite the connecting part (23). For placing the end of the tube-like pressure transmitting part (22) in the main body (30), the attachment part (32) has a recess (32a) which is substantially annular-shaped and dented inwardly in the main body (30), and a projection (32b) projecting in the recess (32a) to fit into the end of the pressure transmitting part (22). A through hole (32c) is formed in the projection (32b) so that the internal pressure generated in the pressure sensing part (21) is transmitted to the pressure receiving part (31) through the pressure transmitting part (22).

The pressure receiving part (31) includes a pressure receiving sensor (33) therein. The pressure receiving sensor (33) is constituted of a microphone, a pressure sensor, or the like. Upon receiving the internal pressure generated in the pressure sensing part (21), the pressure receiving part (31) converts the internal pressure to voltage, and outputs the voltage as a signal to a circuit unit (40) in the main body (30).

The main body (30) includes a box-shaped case and a circuit unit (40) installed in the case. On an upper surface of the case, a power switch (34) for turning on/off the body movement determination system (10) is arranged.

Figure 3:
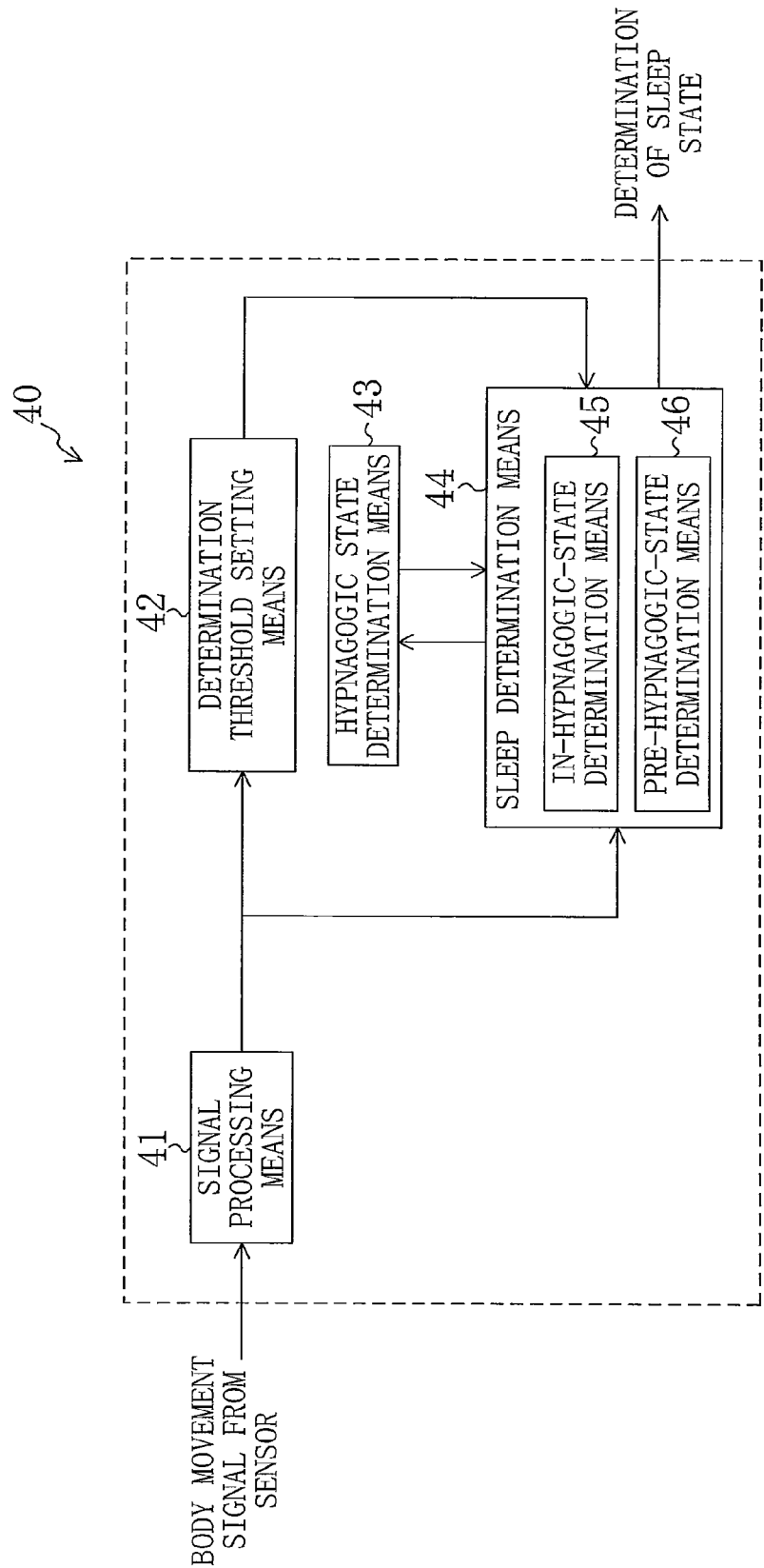
FIG. 3 is a block diagram illustrating the structure of a circuit unit of the sleep determination apparatus.

As shown in FIG. 3, the circuit unit (40) includes a signal processing means (41), a determination threshold setting means (42), a hypnagogic state determination means (43), and a sleep determination means (44).

The signal processing means (41) modulates the detection signal output from the sensor (20) to a signal of a predetermined level and a predetermined frequency band used for the determination threshold setting means (42) and the sleep determination means (44).

Based on the body movement signal modulated by the signal processing means (41), the determination threshold setting means (42) sets and updates a body movement determination threshold which is a boundary level between a large movement signal derived from the subject's coming in/out of the bed, rolling over, and the like, and a small movement signal derived from the subject's respiration and heartbeat. Specifically, the determination threshold setting means (42) calculates in succession a minimum value of the body movement signal processed by the signal processing means (41) every predetermined time (e.g., every 10 seconds), and determines the minimum value as the body movement determination threshold. That is, the determination threshold setting means (42) updates the body movement determination threshold at any time based on the minimum values of the body movement signal in every predetermined time. Thus, according to the present embodiment, the body movement determination threshold is a variable value suitably adjusted in response to variations in minimum value of the body movement signal.

When the sleep determination means (44) described later determines that the subject is asleep for a specified time (e.g., 10 minutes) or longer, the hypnagogic state determination means (43) determines that the subject is in the hypnagogic state. The determination result is sent to the sleep determination means (44) and used for the determination by the sleep determination means (44).

The sleep determination means (44) determines whether the subject is awake or asleep based on a comparison between the body movement signal output from the signal processing means (41) and the determination threshold determined by the determination threshold setting means (42). The sleep determination means (44) is configured to change a method of sleep determination in response to whether the subject is in the hypnagogic state or not determined by the hypnagogic state determination means (43).

Specifically, the sleep determination means (44) includes an in-hypnagogic-state determination means (45) which makes a sleep determination when the hypnagogic state determination means (43) determines that the subject is in the hypnagogic state, and a pre-hypnagogic-state determination means (46) which makes a sleep determination when the hypnagogic state determination means (43) determines that the subject is not in the hypnagogic state.

When the subject is in the hypnagogic state, the in-hypnagogic-state determination means (45) determines that the subject is awake when the body movement signal continuously remains above the determination threshold for the predetermined time or longer, and determines that the subject is asleep in other situations. Therefore, for example, even when noise such as sound of a closing door is generated, an erroneous determination that the subject is awake can be prevented.

When the subject is not yet in the hypnagogic state, the pre-hypnagogic-state determination means (46) determines that the subject is asleep when the body movement signal remains continuously below the determination threshold for the predetermined time or longer, and determines that the subject is awake in other situations. Therefore, for example, even when the subject is making relatively small movement before he enters the hypnagogic state, e.g., reading a book or using a personal computer, an erroneous determination that the subject is asleep can be prevented.

The predetermined time may be set as needed without any limitation. However, it is preferable to set the predetermined time to a period for change in sleep rhythm which is considered most appropriate from a viewpoint of hypnology (about 3 minutes).

—Sleep Determination Operation—

Figure 4:
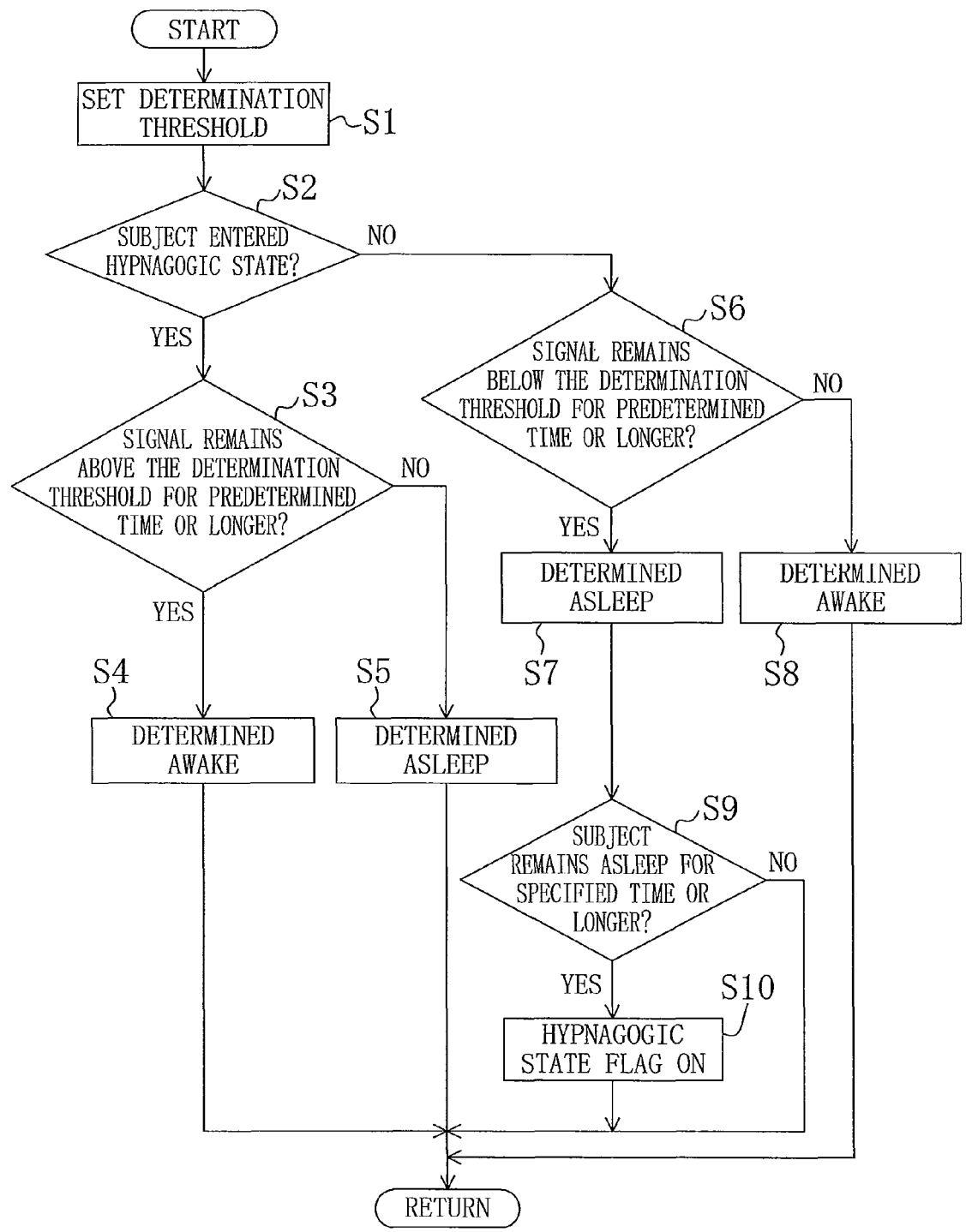
FIG. 4 is a flow chart of sleep determination operation.

Referring to FIGS. 3 to 5, sleep determination operation of the sleep determination apparatus (10) according to the present embodiment will be described as follows.

When the sleep determination apparatus (10) is turned ON, the sensor (20) detects variations in pressure associated with the subject's body movement, and the pressure receiving part (31) of the main body (30) converts the detected pressure variation to an electric signal. The electric signal is output to the circuit unit (40), and modulated to a signal of a predetermined level and a predetermined frequency band by the signal processing means (41).

When the modulated signal is input as the body movement signal to the determination threshold setting means (42), a determination threshold between the small movement signal and the large movement signal is established based on the body movement signal in step S1 shown in FIG. 4. Specifically, a minimum value of the input body movement signal is obtained every given time (e.g., every 10 seconds), and the minimum value is set as the determination threshold by the determination threshold setting means (42). The sensor (20) can reliably detect a small movement signal derived from respiration and heartbeat. Therefore, by setting the minimum value of the body movement signal, i.e., the small movement signal, as the determination threshold, a large movement derived from other body movements than the respiration and heartbeat, if generated, can reliably be discriminated against a small movement.

The body movement signal is also input to the sleep determination means (44) to determine whether the subject is asleep or not based on the body movement signal. A method of the sleep determination is changed depending on whether the subject is in the hypnagogic state or not as shown in FIG. 4 (step S2).

When the subject is in the hypnagogic state (YES is selected in step S2), the in-hypnagogic-state determination means (45) makes a determination whether the input body movement signal continuously remains above the determination threshold for the predetermined time or longer (step S3). When it is determined that the input body movement signal continuously remains above the determination threshold for the predetermined time or longer (YES is selected), the subject is determined as being awake (step S4). Then, operation goes back to START of the flow chart shown in FIG. 4 (return). On the other hand, when the body movement signal does not continuously remain above the determination threshold for the predetermined time or longer, (NO is selected), the subject is determined as being asleep (step S5). Then, operation goes back to START of the flow chart shown in FIG. 4 (return).

When the subject is not in the hypnagogic state (NO is selected in step S2), the pre-hypnagogic-state determination means (46) makes a determination whether the input body movement signal continuously remains below the determination threshold for the predetermined time or longer (step S6). When it is determined the input body movement signal continuously remains below the determination threshold for the predetermined time or longer (YES is selected), the subject is determined as being asleep (step S7). On the other hand, when the body movement signal does not continuously remain below the determination threshold for the predetermined time or longer (NO is selected), the subject is determined as being awake (step S8), and then the operation goes back to START of the flow chart shown in FIG. 4 (return).

When the subject is not in the hypnagogic state and determined as being asleep (step S7), the hypnagogic state determination means (43) determines whether or not the subject's sleep lasts for not shorter than a specified time longer than the predetermined time (step S9). When it is determined that the subject is continuously sleeping for the specified time or longer (YES is selected), the subject is determined as being in the hypnagogic state, and a hypnagogic state flag is set ON (step S10). When it is determined that the subject's sleep does not last for the specified time or longer (NO is selected), the subject is determined as not being in the hypnagogic state. Then, the operation goes back to START of the flow chart shown in FIG. 4 (return).

An example of sleep determination by the above-described sleep determination operation is shown in FIGS. 5(a) and 5(b). FIG. 5(a) schematically shows sleep determination results in a period from when the subject goes to bed to when the subject enters the hypnagogic state. FIG. 5(b) schematically shows sleep determination results after the subject entered the hypnagogic state. For comparison, levels of the subject's body movement before and after entering the hypnagogic state are the same, and the determination threshold is unchanged before and after entering the hypnagogic state. In the examples shown in FIGS. 5(a) and 5(b), the sleep determination apparatus (10) is configured to output the body movement level every 1 minute.

Before the subject enters the hypnagogic state, it is determined that the subject is asleep when the body movement level continuously remains below the determination threshold for the predetermined time (3 minutes) or longer, and that the subject is awake in other situations. Therefore, as shown in FIG. 5(a), even when the body movement level falls below the determination threshold, it is determined that the subject is awake (indicated with blank circles) as long as the body movement level does not continuously remain below the determination threshold continuously for 3 minutes or longer. Specifically, when the subject is not yet in the hypnagogic state, whether the subject is asleep or not is determined more stringently, and the subject is determined as being awake when the body movement level exceeds the determination threshold only slightly. Therefore, when the subject is making relatively small movement on the bed before entering the hypnagogic state, e.g., reading a book or using a personal computer, an erroneous determination that the subject is asleep can be prevented.

In contrast, after the subject entered the hypnagogic state, it is determined that the subject is awake when the body movement level continuously remains above the determination threshold for the predetermined time (3 minutes) or longer, and that the subject is asleep in other situations. Therefore, as shown in FIG. 5(b), even when the body movement level exceeds the determination threshold, it is determined that the subject is asleep (indicated with solid circles) as long as the body movement level does not constantly remain above the determination threshold for 3 minutes or longer. Specifically, after the subject entered the hypnagogic state, whether the subject is awake or not is determined more stringently, and the subject is determined as being asleep when the body movement level falls below the determination threshold only slightly. Therefore, even when noise such as sound of a closing door is generated after the subject entered the hypnagogic state, the determination is not affected by the noise. Thus, an erroneous determination that the subject is awake can be prevented.

That is, as described above, the sleep determination method is changed before and after the subject entered the hypnagogic state. Therefore, the sleep determination results before and after the subject entered the hypnagogic state are different as shown in FIGS. 5(a) and 5(b), though they are based on the same body movement level. Whether the subject is asleep or not is determined stringently before the subject enters the hypnagogic state, while whether the subject is awake or not is determined stringently after the subject entered the hypnagogic state. Thus, the occurrences of erroneous determination due to noise and small body movements can be reduced.

Figure 6:
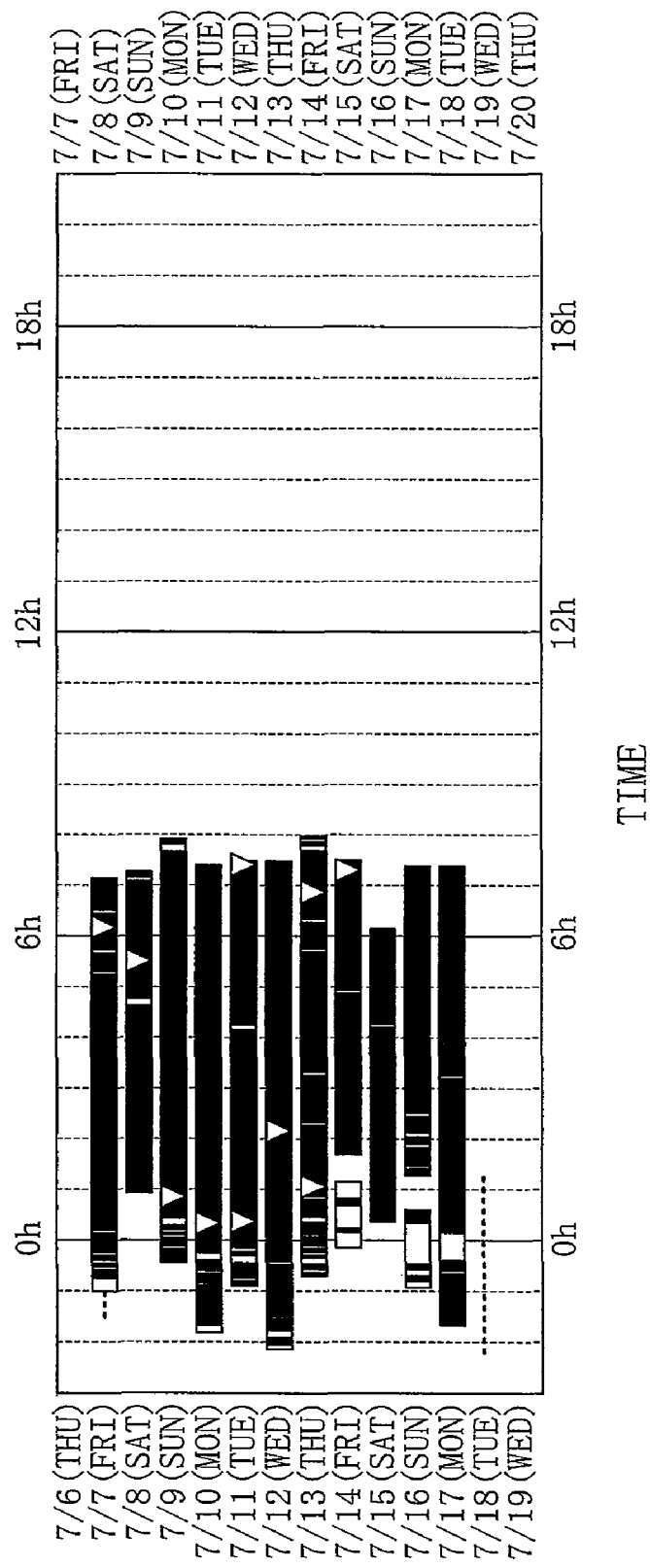
FIG. 6 is a graph illustrating an example of sleep determination results obtained by a conventional sleep determination method.
Figure 7:
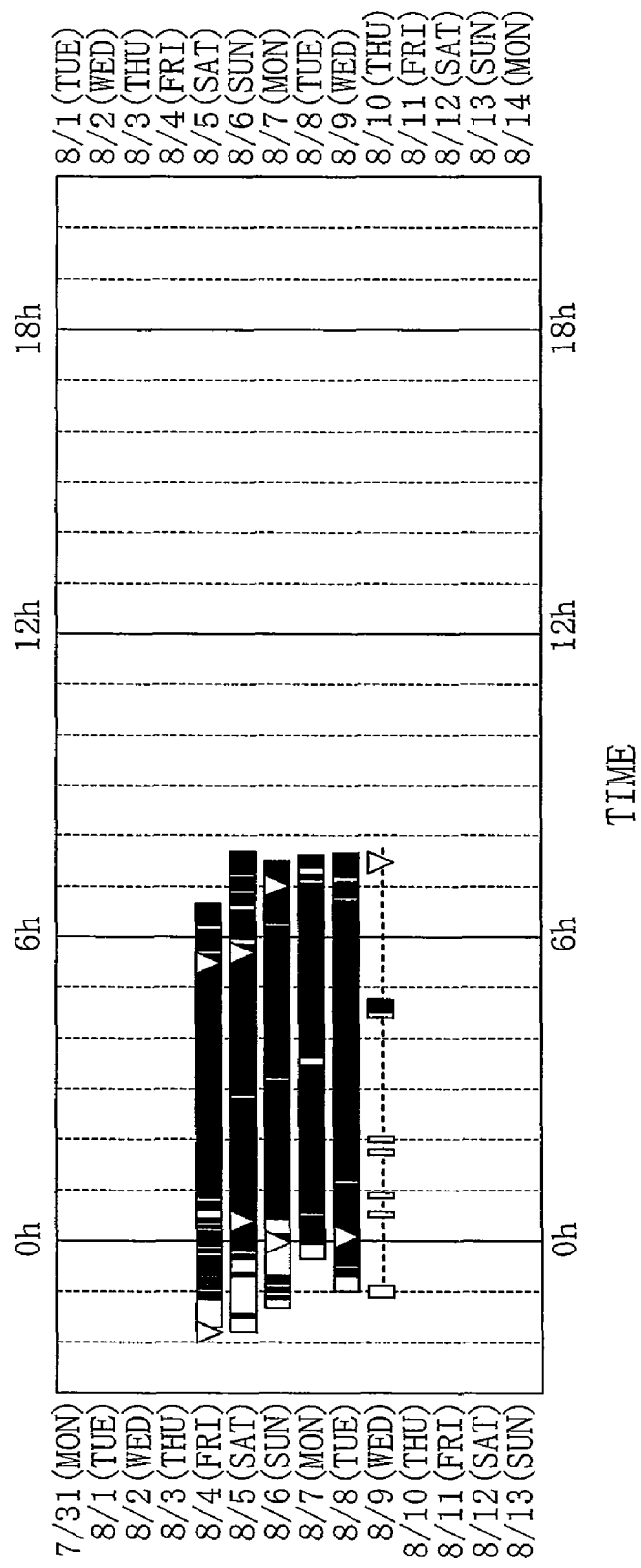
FIG. 7 is a graph illustrating an example of sleep determination results obtained by a sleep determination method of the present invention.

The sleep determination results obtained by the above-described sleep determination method are compared with the determination results obtained by the conventional method to confirm determination accuracy. FIG. 6 shows data of the subject's sleep determined by the conventional determination method, and FIG. 7 shows data of the subject's sleep determined by the above-described determination method. Based on FIGS. 6 and 7, FIG. 8 shows a comparison between a period of actual wakefulness before the subject enters the hypnagogic state (a period from when the subject goes to bed to when the subject enters the hypnagogic state) and a period of wakefulness before the subject enters the hypnagogic state determined by the sleep determination method, and the resulting rate of accurate wakefulness determination.

In FIGS. 6 and 7, a blank part indicates a wakefulness state, a solid part indicates a sleep state, and a dotted line indicates that the subject is not present in the bed. A downward pointed triangle indicates time when the subject turned a switch ON immediately before entering the hypnagogic state. In FIGS. 6 and 7, it is considered that the subject turned the switch ON almost immediately before entering the hypnagogic state on $9^{th}$ to $11^{th}$, and $13^{th}$ July as shown in FIG. 6, and on $5^{th}$, $6^{th}$, and $8^{th}$ August as shown in FIG. 7. Therefore, based on these data, a comparison is made between a period of actual wakefulness before the subject enters the hypnagogic state and the determination results by the above-described sleep determination method.

As shown in FIG. 8, a period of wakefulness determined by the conventional sleep determination method is about 30% of a period (B–A) from when the subject enters the bed to when the subject enters the hypnagogic state. In this method, the rate of correct determination is low. In contrast, a period of wakefulness determined by the sleep determination method of the present invention is about 65% of the period of actual wakefulness. In this method, the rate of correct wakefulness determination is more than twice the rate obtained by the conventional method. Thus, FIG. 8 indicates that the sleep determination method of the present invention is higher in determination accuracy than the conventional sleep determination method.

—Effect of the Embodiment—

In the present embodiment described above, when the subject is not yet in the hypnagogic state, it is determined that the subject is asleep when the body movement signal associated with the subject's body movement remains continuously below the determination threshold for the predetermined time, and that the subject is awake in other situations. Therefore, even when the subject before entering the hypnagogic state is making small body movement, e.g., reading a book or using a personal computer, the subject is not erroneously determined as being asleep. Instead, the subject can be determined as being awake with higher accuracy, as compared with the conventional method in which the subject is determined as being awake when the body movement signal continuously remains above the determination threshold for the predetermined time.

Specifically, in the structure where a minimum value of the body movement signal in a given period is updated as the determination threshold at any time, the erroneous determination that the subject is asleep, though he is actually reading a book or using a personal computer on the bed before entering the hypnagogic state, can reliably be prevented by the above-described stringent determination whether the subject is asleep or not.

After the subject entered the hypnagogic state, it is determined the subject is awake when the body movement signal continuously remains above the determination threshold for the predetermined time, and that the subject is asleep in other situations, in the same manner as the conventional method. Therefore, when the subject is in the hypnagogic state, wakefulness of the subject can accurately be detected without greatly being affected by noise.

When it is determined that the subject is continuously asleep for the specified time or longer, the subject is determined as being in the hypnagogic state. Therefore, whether the subject is in the hypnagogic state or not can accurately be determined. This allows an accurate determination of the subject's sleep even though the determination method is changed before and after entering the hypnagogic state as described above.

OTHER EMBODIMENTS

The above-described embodiment may be configured as follows.

For example, in the above-described embodiment, the sleep determination method is changed before and after the subject enters the hypnagogic state. However, the present invention is not limited thereto, and the same sleep determination method may be used before and after the hypnagogic state. In this case, the subject who is asleep may erroneously be determined as being awake with high probability due to noise generated after the subject entered the hypnagogic state, or the like.

In the above-described embodiment, the body movement determination threshold is set and updated at any time based on the body movement signal. However, the determination threshold may be a fixed value determined in advance based on experiments and empirical rules.

The sleep determination apparatus (10) described above is used for health care of the subject. However, for example, the body movement measurement system may be applied to a sleeping capsule in which air conditioning is performed in response to the state of a sleeping subject.

INDUSTRIAL APPLICABILITY

Thus, as described above, the present invention is useful for a sleep determination apparatus which determines whether a subject is asleep or not based on a body movement signal associated with the subject's body movement.

The invention claimed is:

1. A sleep determination apparatus comprising:
 a body movement detection device disposed outside a body of a subject and which is attached to a bedding to detect body movement of the subject and output the body movement as a body movement signal;
 a first sleep determination device which determines that the subject is asleep when the body movement signal continuously remains below a determination threshold for a predetermined time or longer, and that the subject is awake when a condition that the body movement signal continuously remains below the determination threshold for the predetermined time or longer is not satisfied;
 a sleep onset determination device which determines that sleep onset of the subject has occurred when the first sleep determination device makes a determination continuously for a predetermined time or longer that the subject is asleep; and
 a second sleep determination device which determines in place of the first sleep determination device, when the sleep onset determination device determines that sleep onset of the subject has occurred, that the subject is awake when the body movement signal continuously remains above a determination threshold for a predetermined time or longer, and that the subject is asleep when a condition that the body movement signal continuously remains above the determination threshold for the predetermined time or longer is not satisfied,
 wherein the first sleep determination device, the sleep onset determination device, and the second sleep determination device are disposed in the apparatus.

2. The sleep determination apparatus of claim 1, wherein the predetermined time is 3 minutes.

3. The sleep determination apparatus of claim 1, further comprising:
 a determination threshold setting device which sets and updates the determination threshold based on a minimum value of the body movement signal in every given time.

* * * * *